US010968116B2

(12) United States Patent
Bergqvist et al.

(10) Patent No.: US 10,968,116 B2
(45) Date of Patent: Apr. 6, 2021

(54) LIQUID TREATMENT SYSTEM

(71) Applicant: Wallenius Water Innovation AB, Stockholm (SE)

(72) Inventors: Johan Bergqvist, Saltsjo-Boo (SE); David Skantze, Saltsjo-Boo (SE)

(73) Assignee: Wallenius Water Innovation AB, Stockholm (SE)

( * ) Notice: Subject to any disclaimer, the term of this patent is extended or adjusted under 35 U.S.C. 154(b) by 0 days.

(21) Appl. No.: 16/485,970

(22) PCT Filed: Feb. 16, 2018

(86) PCT No.: PCT/SE2018/050149
§ 371 (c)(1),
(2) Date: Aug. 14, 2019

(87) PCT Pub. No.: WO2018/151658
PCT Pub. Date: Aug. 23, 2018

(65) Prior Publication Data
US 2020/0231469 A1 Jul. 23, 2020

(30) Foreign Application Priority Data
Feb. 17, 2017 (SE) .................................. 1750161-0

(51) Int. Cl.
*C02F 1/00* (2006.01)
*C02F 1/32* (2006.01)
(Continued)

(52) U.S. Cl.
CPC ................ *C02F 1/325* (2013.01); *A61L 2/10* (2013.01); *A61L 2/26* (2013.01); *B08B 9/023* (2013.01);
(Continued)

(58) Field of Classification Search
USPC ........................................................ 250/431
See application file for complete search history.

(56) References Cited

U.S. PATENT DOCUMENTS 2,670,439 A * 2/1954 Darney ................... C02F 1/325
250/429
4,017,734 A * 4/1977 Ross ......................... A61L 2/10
250/431
(Continued)

FOREIGN PATENT DOCUMENTS

EP 0785907 B1 8/1999
EP 1371611 A1 12/2003
(Continued)

OTHER PUBLICATIONS

International Search Report PCT/ISA/210 for International Application No. PCT/SE2018/050149 dated Feb. 16, 2018.
(Continued)

*Primary Examiner* — Phillip A Johnston
(74) *Attorney, Agent, or Firm* — Harness, Dickey & Pierce, P.L.C.

(57) ABSTRACT

A liquid treatment system comprising at least one ultraviolet light treatment lamp arranged within an elongated protective UV-transparent sleeve provided along a central longitudinal axis A, said sleeve having an outer surface and an essentially circular cross-sectional shape; and an elongated reactor configured to receive said sleeve, whereby an elongated liquid treatment chamber for receiving liquid to be treated, is provided between an inner surface of the reactor and the outer surface of the sleeve; wherein said liquid treatment system further comprises at least one elongated cleaning device provided side by side with the sleeve within the liquid treatment chamber and along at least a part of the length of the elongated sleeve, wherein said at least one cleaning device is compressed towards the outer surface of
(Continued)

the sleeve by the reactor, and wherein at least one of the sleeve and the reactor is configured to rotate around the longitudinal axis A such that the at least one cleaning device will be touching and cleaning the outer surface of the sleeve over essentially the whole circumference of the sleeve.

14 Claims, 8 Drawing Sheets

(51) Int. Cl.
*A61L 2/10* (2006.01)
*A61L 2/26* (2006.01)
*B08B 9/023* (2006.01)
*B08B 9/027* (2006.01)

(52) U.S. Cl.
CPC ............ *B08B 9/027* (2013.01); *A61L 2202/11* (2013.01); *A61L 2202/122* (2013.01); *C02F 2201/324* (2013.01); *C02F 2201/3223* (2013.01)

(56) References Cited

U.S. PATENT DOCUMENTS

| | | | |
|---|---|---|---|
| 4,766,321 A * | 8/1988 | Lew | A61L 9/20 210/760 |
| 5,227,140 A | 7/1993 | Hager et al. | |
| 5,528,044 A * | 6/1996 | Hutchison | C02F 1/325 250/431 |
| 5,937,266 A | 8/1999 | Kadoya | |
| 5,942,110 A * | 8/1999 | Norris | C02F 1/325 210/198.1 |
| 6,570,167 B1 * | 5/2003 | Bryer | G01C 15/002 250/431 |
| 7,159,264 B2 | 1/2007 | Sotirakos et al. | |
| RE39,522 E | 3/2007 | Ishiyama | |
| 10,696,568 B2 * | 6/2020 | Henderson | B01F 5/0057 |
| 2001/0032659 A1 | 10/2001 | Wang et al. | |
| 2006/0123571 A1 | 6/2006 | Sotirakos et al. | |

FOREIGN PATENT DOCUMENTS

| | | |
|---|---|---|
| EP | 1714944 A1 | 10/2006 |
| GB | 710903 A | 6/1954 |
| GB | 2389577 A | 12/2003 |
| GB | 2529041 A | 2/2016 |
| KR | 20100044762 A | 4/2010 |
| WO | WO-2016/020693 A1 | 2/2016 |

OTHER PUBLICATIONS

Swedish Search Report for Swedish Patent Application No. 1750161-0 dated Sep. 7, 2017.

* cited by examiner

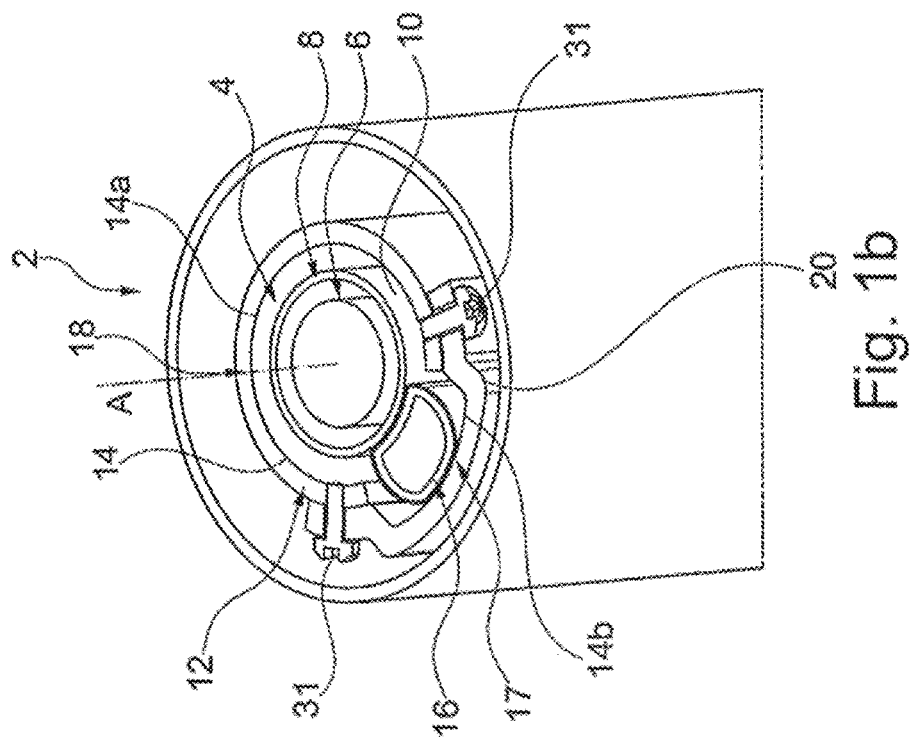
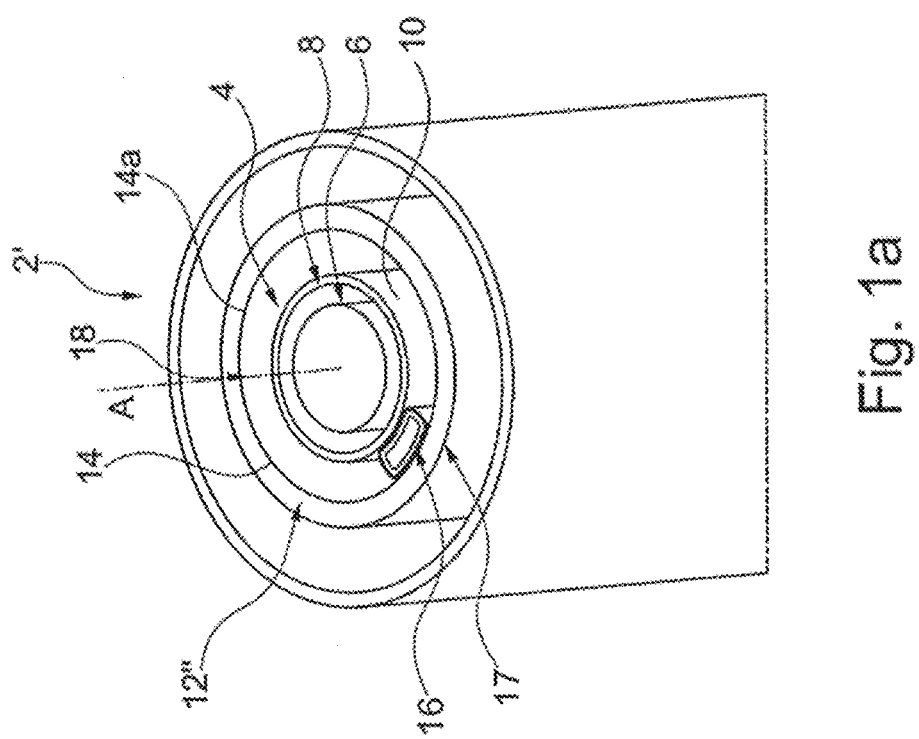

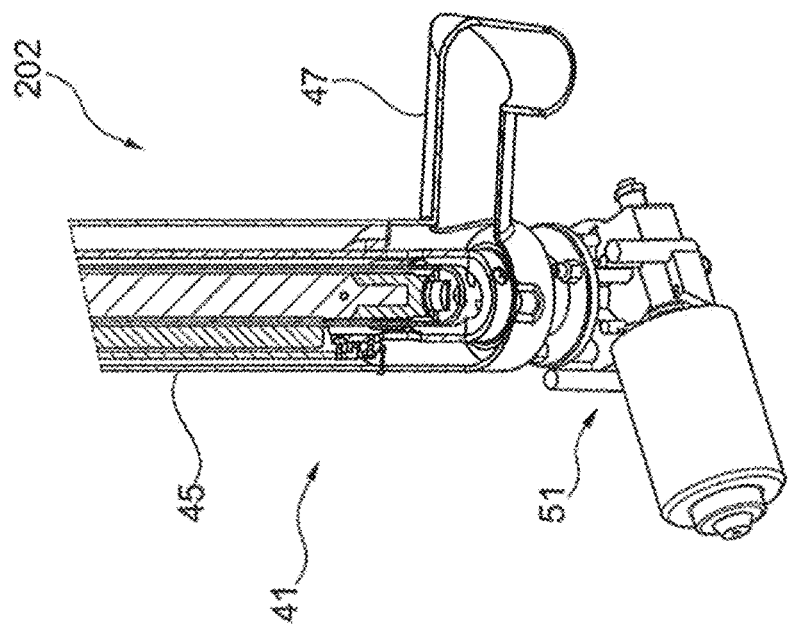
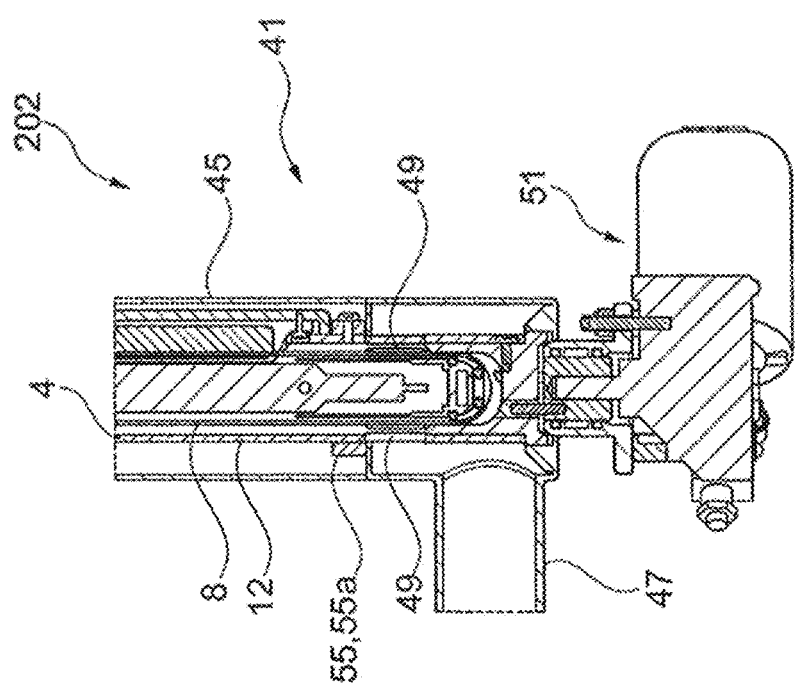
Fig. 5
Fig. 4

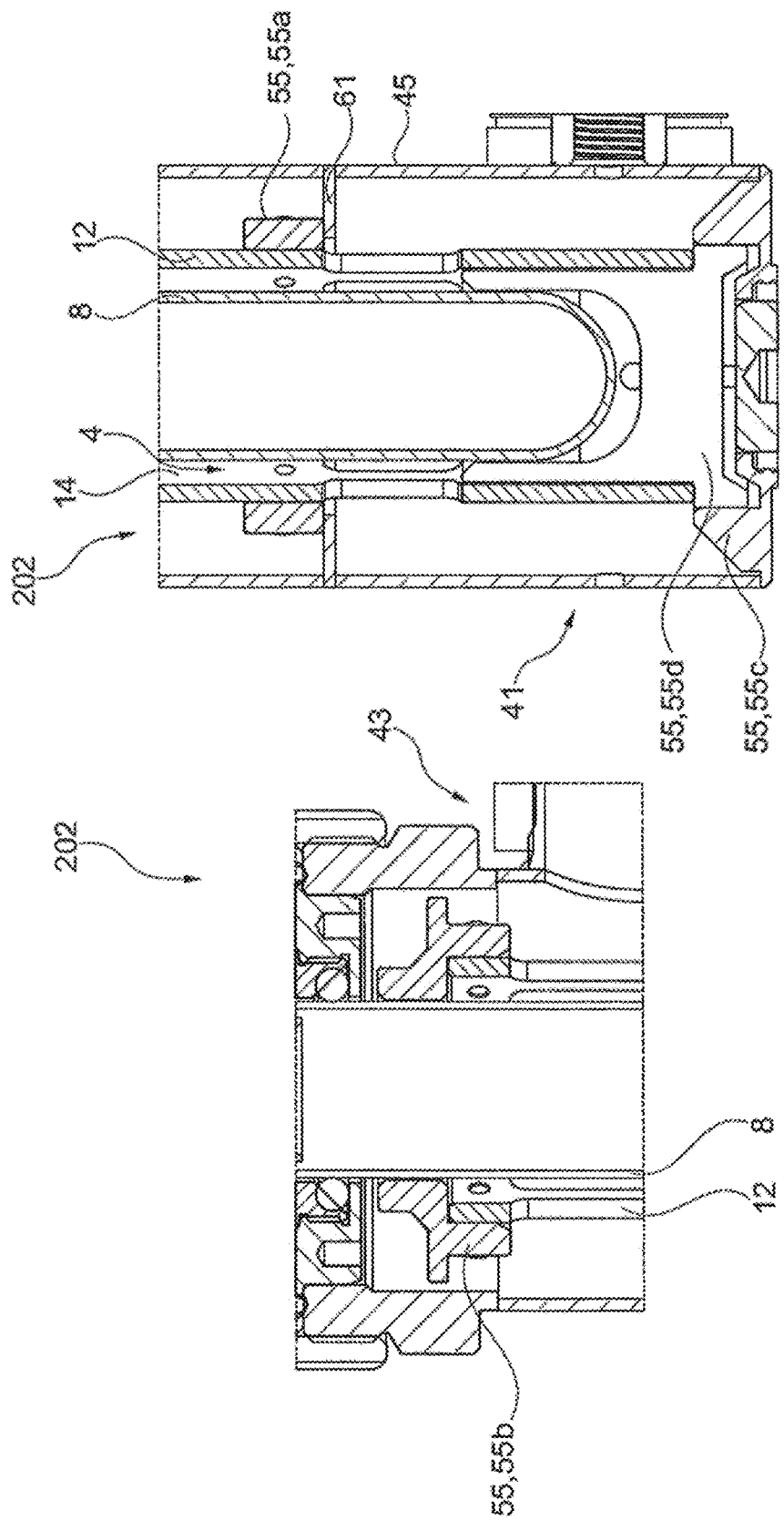

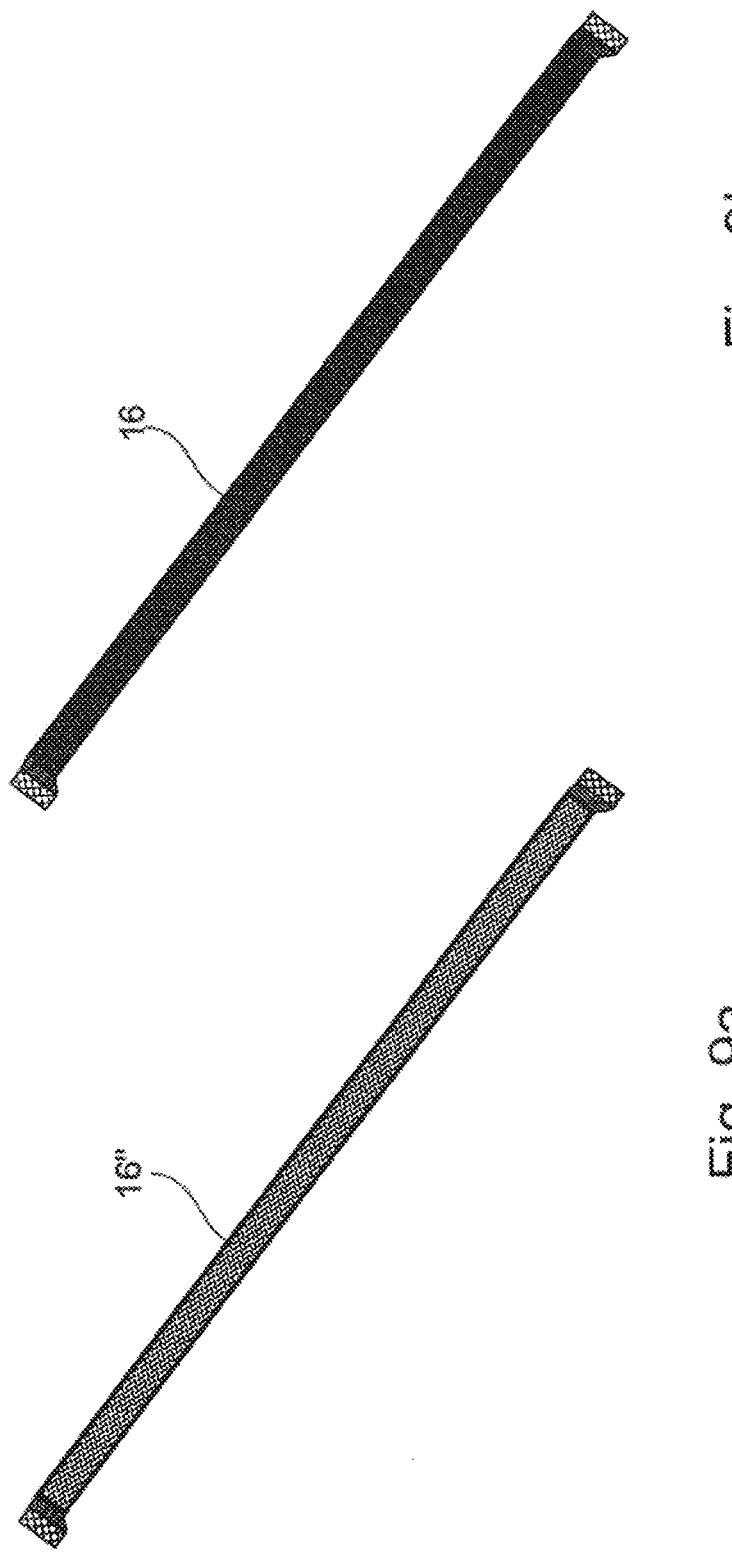

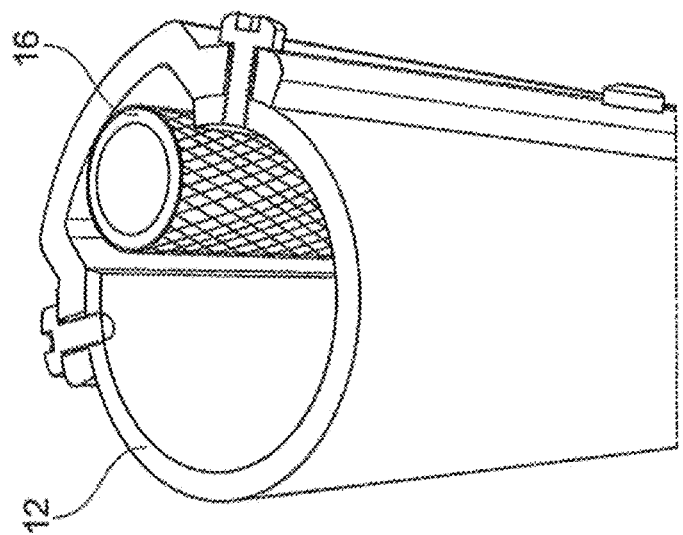
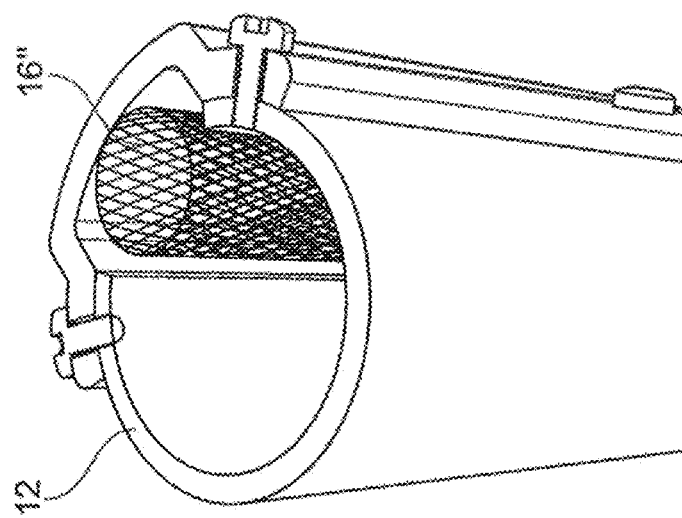

LIQUID TREATMENT SYSTEM

CROSS-REFERENCE TO RELATED APPLICATIONS

This application is a national phase under 35 U.S.C. § 371 of PCT International Application No. PCT/SE2018/050149 which has an international filing date of Feb. 16, 2018, which claims priority to Swedish Application No. 1750161-0, filed Feb. 17, 2017, the entire contents of each of which are hereby incorporated by reference.

TECHNICAL FIELD OF THE INVENTION

The present invention relates to a liquid treatment system comprising at least one ultra-violet (UV) light treatment lamp.

RELATED ART

There are many applications where UV light sources are used for treating liquids. Wallenius Water AB in Sweden has developed and is selling liquid treatment equipment comprising an elongated tubular treatment chamber with an inlet and an outlet. In the treatment chamber at least one generally tubular protective UV transparent sleeve (e.g. made from fused quartz) is arranged and inside the sleeve is a UV light source arranged, such as a lamp capable of generating wavelengths in the UV region.

Another type of treatment reactor developed by the applicant also comprises a treatment chamber having oppositely arranged in- and outlets, where the UV light sources are arranged in elongated sleeves, e.g. fused quartz sleeves. These sleeves are arranged perpendicular to the flow of liquid to be treated through the treatment chamber.

The above described treatment units are functioning very well for treating all sorts of liquids for example water, where the latter described treatment unit is specially adapted for treatment of ballast water in ships. The liquid that is treated often comprises particles and other solid matter other than the organisms that are killed off by the treatment units. These particles, as well as other residue from the killed off organisms, have a tendency to stick on the interior surfaces of treatment units. These particles, and other residue, aggregated on the surface are generally denoted as fouling.

UV light treatment, more specifically UV-light in combination with heat, sometimes provokes chemical reactions resulting in depositions on the interior surfaces. These resulting depositions are generally denoted as scaling.

Often scaling is more difficult to remove from the surface than fouling.

This means that in order to have an optimum efficiency of the treatment device the interior has to be cleaned regularly. According to one solution in the prior art cleaning is performed by injecting cleaning liquids into the treatment chamber, where the cleaning liquids are developed for removing the fouling or scaling on the surfaces. However, even if they are efficient for removing fouling/scaling and the like deposits on the surfaces of the treatment chambers, they require that the treatment units are closed down during a period of time, whereby thus no treatment of liquid may be performed.

According to other suggestions, various forms of wiper mechanisms have been designed to remove fouling/scaling from surfaces. All such forms of wiper mechanisms act to "wipe off" the layer from the external surface of the sleeve. Such wiper mechanisms often require a large annular space between the outside surface of the sleeve housing the UV lamp and the surrounding tubing housing the sleeve in order to accommodate the wiper mechanism. The treatment system relies on the transmittance of the liquid in order to allow the UV photons to reach the contaminants in the liquid passing through the annular region between the sleeve and housing.

Some patents and patent applications within the technical field will now be briefly discussed in the following.

EP1371611 relates to a fluid treatment apparatus. A cleaning assembly comprising a plurality of cleaning heads is provided. The cleaning heads each comprise a plurality of portions of titanium dioxide which are biased against the surface of the respective UV lamps.

U.S. Pat. No. 5,227,140 relates to a modular self-cleaning oxidation chamber comprising a shuttling scraper including an annular wiper that simultaneously cleans the inside surface of the surrounding tubular module as well as the outside surface of an enclosed quartz tube. The wiper is driven by the liquid and has the form of an annular disk and being composed of a fluoroelstomer.

EP1714944 relates to a fluid disinfection apparatus of a kind similar to the apparatus of EP1371611. A cleaning material may be a fabric or metal, e.g. a metal gauze covered by titanium dioxide and may be biased into contact with the ultra-violet light source.

U.S. Pat. No. 7,159,264 discloses a scraper for cleaning tubular members. The scraper comprises a plurality concatenated resilient segments adapted to contact the exterior surface the tubular member. The resilient member is made up from a resilient wire. The cleaning effect of the tubular member is achieved when the scraper is moved axially with regard to the tubular member.

USRE39522 relates to ultraviolet ray irradiation equipment having scraper rings fitted to light transmission tubes. The scraper ring defines a cleaning solution chamber to be in contact with the outer surface of a tube. The scraper may be made from a non-elastic material such as Teflon® and stainless steel. The frequency of cleaning is determined upon the quantity of scale and is exemplified as two to three times a day.

U.S. Pat. No. 5,937,266 relates to a light irradiating device equipped with a cleaning mechanism. The mechanism comprises scrapers adapted to slide along the outside surface of the light-transmitting tubes. The material used for the scraper may rubber or Teflon®, or a cleaning cloth.

EP0785907 relates to a shuttling scraper including a wiper cartridge, configured to clean the outside surface of a quartz tube. The cartridge may be filled with a scrubber material which may consist of stainless steel turnings or stainless steel wool. When the shuttling scraper is in a parked position the wiper cartridge is protected from UV radiation and the heat of the UV lamp, which also helps to extend the life of the wiper cartridge.

The above prior art documents disclose various UV-light treatment apparatuses that include mechanical cleaning members provided with various materials for removing fouling/scaling from a UV-lamp surface.

Despite the various solutions suggested in the above prior art some drawbacks still remain in particular with regard to remove harder material, i.e. scaling, from the outer surface of the UV-transparent sleeve enclosing the UV-lamp. Furthermore, when including a wiper mechanism in the treatment chamber the size of the treatment chamber needs to be big enough to house the wiper mechanism. As the size of the annular region between the sleeve and tubing surrounding the sleeve increases, the effectiveness of the UV light at the outer edges of the annulus region may decrease, which may impact the efficiency of the system, especially when treating opaque liquids.

SUMMARY

An object of the present invention is to provide an improved liquid treatment system provided with means capable of efficiently removing harder material from the outer surface of the sleeve.

This is achieved in a liquid treatment system according to claim 1.

In one aspect of the invention a liquid treatment system is provided comprising:
- at least one ultra-violet (UV) light treatment lamp arranged within an elongated protective UV-transparent sleeve provided along a central longitudinal axis A, said sleeve having an outer surface and an essentially circular cross-sectional shape; and
- an elongated reactor configured to receive said sleeve, whereby an elongated liquid treatment chamber for receiving liquid to be treated, is provided between an inner surface of the reactor and the outer surface of the sleeve; wherein said liquid treatment system further comprises
- at least one elongated cleaning device provided side by side with the sleeve within the liquid treatment chamber and along at least a part of the length of the elongated sleeve, wherein said at least one cleaning device is compressed towards the outer surface of the sleeve by the reactor, and wherein at least one of the sleeve and the reactor is configured to rotate around the longitudinal axis A such that the at least one cleaning device will be touching and cleaning the outer surface of the sleeve over essentially the whole circumference of the sleeve.

Hereby, by providing an elongated cleaning device along the length of the sleeve and providing the cleaning device within the reactor and rotate the reactor or the sleeve in order to transfer the cleaning device over the circumference of the sleeve outer surface a convenient and effective cleaning process is achieved. In this device there is no need to transfer a cleaning unit up and down along the sleeve. A rotation of the sleeve or the reactor is all that is needed.

In one embodiment the reactor has a partly circular cross-sectional shape with at least one part having an extended radius where the at least one cleaning device is provided.

Hereby by providing the cleaning device in a part of the reactor having an extended radius it is possible to keep the distance between the outer surface of the sleeve and the inner surface of the rest of the reactor even smaller. Hereby, by keeping this distance small the UV light will better reach all the liquid within the treatment chamber and even opaque liquid can be treated effectively. Furthermore it may be hard to produce an elongated sleeve from fused quartz with exact dimensions. Because of this problem with tolerances in fused quartz the distance between the outer surface of the sleeve and the inner surface of the reactor may differ throughout the length of the sleeve. Hereby this solution where the cleaning device, also called the wiper, is provided within a part of the reactor having extended radius will ensure that the cleaning device will not get stuck in a smaller passage when one of the sleeve or the reactor is rotating. At the same time this solution makes it possible to keep the distance between the sleeve outer surface and the reactor inner wall as small as possible which is especially advantageous when treating opaque liquids as described above.

In one embodiment of the invention the reactor comprises for each cleaning device:
- a first part having a cross sectional shape being essentially a part of a circle, which circle is centered around the longitudinal axis A, and
- a second part configured for holding the cleaning device and connected to the first part,
- wherein an inner surface of the first part and an inner surface of the second part together encircle the outer surface of the sleeve, wherein the inner surface of the second part being provided at a greater distance from the outer surface of the sleeve than the inner surface of the first part is.

In one embodiment of the invention either the sleeve or the elongated reactor is rotated either in one direction or back and forth around the longitudinal axis A such that the at least one cleaning device will be touching and cleaning the outer surface of the sleeve over the whole circumference of the sleeve.

In one embodiment of the invention the liquid treatment system further comprises a surface bearing arrangement configured for keeping the sleeve and the reactor axially and radially aligned while allowing at least one of the sleeve and the reactor to rotate around the longitudinal axis A.

In one embodiment of the invention two cleaning devices are provided, one for one part of the length of the elongated sleeve and the other for the rest of the length of the elongated sleeve, whereby the two cleaning devices are provided diametrically opposite each other within the reactor, one on each side of the sleeve.

In one embodiment of the invention two cleaning devices are provided, one on one side of the sleeve and the other on the opposite side of the sleeve.

In one embodiment of the invention the at least one cleaning device comprises a metal braid.

In one embodiment of the invention the metal braid is a hollow cylinder which is braided, knitted or woven from a metallic material.

In one embodiment of the invention the metal braid is abrasive and the metallic material is resistant to UV light and corrosion.

In one embodiment of the invention the metallic material is stainless steel, monel or titanium.

In one embodiment of the invention the metal braid is a hollow cylinder and comprises an elastic inner tube.

In one embodiment of the invention the elongated cleaning device comprises an elongated cleaning part from abrasive material provided closest to the outer surface of the sleeve and an elongated elastic part provided closest to the inner surface of the reactor.

In one embodiment of the invention the cleaning part is a metal braid or steel wool and the elastic part is a spring, foam rubber, silicon rubber or a flexible tube.

In one embodiment of the invention the elongated cleaning device comprises an elongated elastic, abrasive material.

BRIEF DESCRIPTION OF THE DRAWINGS

FIG. 1a shows schematically a transversal cross section of a liquid treatment system according to one embodiment of the invention.

FIG. 1b shows schematically a transversal cross section of a liquid treatment system according to another embodiment of the invention.

FIG. 4 is a cross section of a first end of a liquid treatment system according to one embodiment of the invention.

FIG. 5 is a side view, partly in cross section of the first end of the same liquid treatment system as shown in FIG. 4.

FIG. 7 is a cross section of the second end of the same liquid treatment system as shown in FIGS. 4-6.

FIG. 8 is a cross section of the first end of the same liquid treatment system as shown in FIGS. 4-7.

FIGS. 9a and 9b show two different examples of cleaning devices to be used in systems according to embodiments of the invention.

FIGS. 10a and 10b show a reactor according to one embodiment of the invention comprising the two different cleaning devices as shown in FIGS. 9a and 9b.

DETAILED DESCRIPTION OF THE INVENTION

Figure 2:
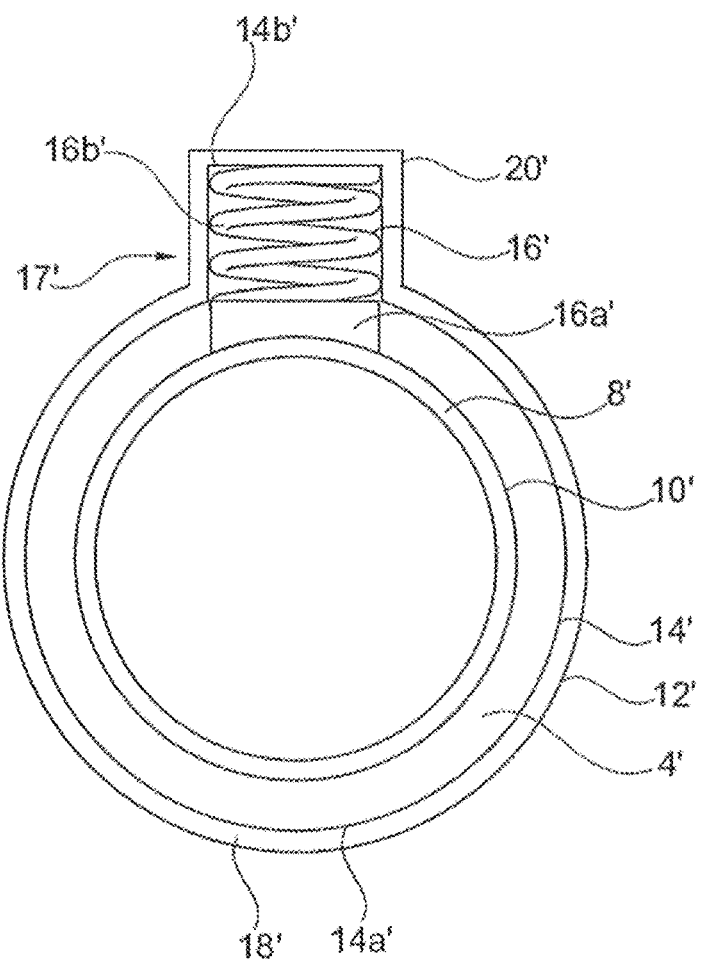
FIG. 2 shows schematically some details in a transversal cross section of a liquid treatment system according to another embodiment of the invention.

The invention relates to a liquid treatment system 2, 2'; 102, 202 as shown in The FIGS. 1-8. The same or similar features in the different embodiments are given the same or similar reference numbers and the following description is referring to all of the FIGS. 1-8. A liquid treatment system according to the invention comprises at least one ultra-violet (UV) light treatment lamp 6 arranged within an elongated protective UV-transparent sleeve 8; 8' provided along a central longitudinal axis A. Said sleeve 8; 8' has an outer surface 10; 10' and an essentially circular cross-sectional shape. The liquid treatment system 2, 102, 202 comprises further an elongated reactor 12; 12'; 12" configured to receive said sleeve 8; 8'. Hereby an elongated liquid treatment chamber 4; 4' for receiving liquid to be treated, is provided between an inner surface 14; 14' of the reactor 12; 12'; 12" and the outer surface 10; 10' of the sleeve 8; 8'.

Figure 3:
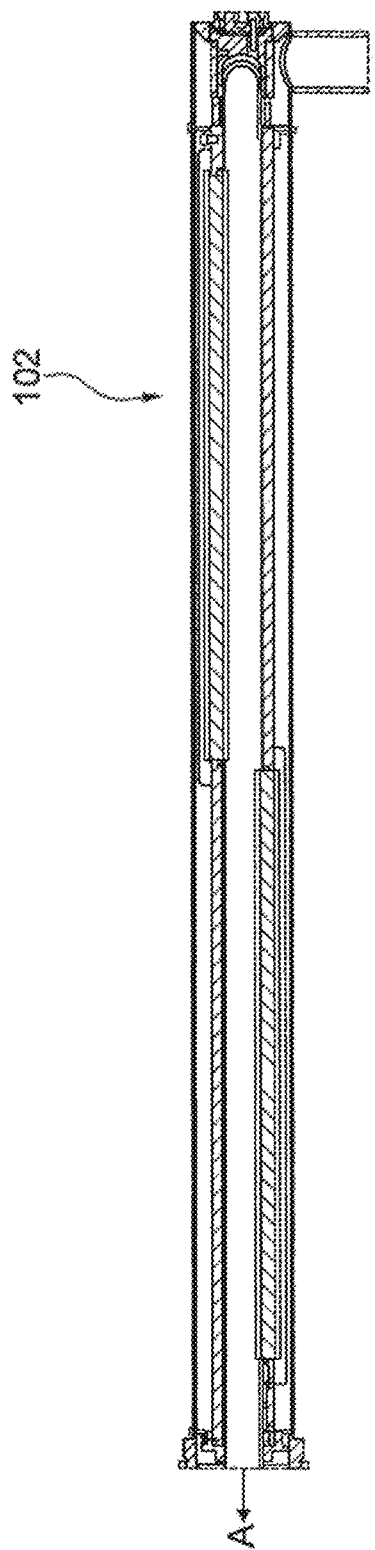
FIG. 3 is a longitudinal cross section of a liquid treatment system according to one embodiment of the invention.

According to the invention said liquid treatment system 2, 2'; 102, 202 further comprises at least one elongated cleaning device 16; 16' provided side by side with the sleeve 8; 8' within the liquid treatment chamber 4; 4' and along at least a part of the length of the elongated sleeve 8; 8'. In one embodiment of the invention one single elongated cleaning device 16; 16' is provided along essentially the whole length of the sleeve 8; 8'. However in another embodiment of the invention two cleaning devices 16; 16' are provided, one for one part of the length of the elongated sleeve 8, 8' and the other for the rest of the length of the elongated sleeve, whereby the two cleaning devices 16; 16' are provided diametrically opposite each other within the reactor 12; 12'; 12", one on each side of the sleeve 8; 8'. This is shown in FIG. 3 and one reason for providing two cleaning devices 16; 16' instead of one and diametrically opposite each other is because hereby the stress on the glass will be decreased. Either each one of the two cleaning devices 16; 16' can be provided along the whole length of the sleeve but diametrically opposite each other or alternatively as described above one cleaning device 16; 16' can be provided for one part of the sleeve and the other for the rest of the sleeve.

Furthermore according to the invention said at least one cleaning device is compressed towards the outer surface 10; 10' of the sleeve 8; 8' by the reactor 12; 12'; 12". This is best shown in FIGS. 1a, 1b and 2. Furthermore at least one of the sleeve and the reactor is configured to rotate around the longitudinal axis A. Either the sleeve 8; 8' or the elongated reactor 12; 12'; 12" is rotated and they can rotate either in one direction or back and forth around the longitudinal axis A such that the at least one cleaning device 16; 16' will be touching and cleaning the outer surface 10; 10' of the sleeve 8; 8' over the whole circumference of the sleeve 8; 8'. Holding the cleaning device and compressing it towards the sleeve by the reactor itself while rotating either the sleeve or the reactor provides a convenient and space efficient method for cleaning the sleeve compared to many prior art methods using annular cleaning units which are moved up and down along the sleeve.

In some embodiments the cleaning device 16; 16' needs to be fastened to the reactor 12; 12'; 12" in some suitable way (not shown). For example the cleaning device 16; 16' can be clamped to the reactor 12; 12'; 12" wall in one or both ends of the liquid treatment system. Other methods for fastening the cleaning device to the reactor can be gluing or screwing at one or more positions along the length of the cleaning device 16; 16'.

FIG. 1a shows a liquid treatment system 2' according to one embodiment of the invention where the reactor 12" is cylindrical and centered around the axis A. The cleaning device 16 is compressed towards the sleeve outer surface 10 by the reactor 12". In this embodiment the cleaning device 16 needs to be secured to the reactor 12" in a suitable way as described above. Hereby the cleaning device 16 will be transferred over the sleeve outer surface 10 when either the sleeve 8 or the reactor 12" is rotated and the sleeve outer surface will be cleaned by the cleaning device 16.

When treating non opaque fluids the distance between the reactor inner wall 14 and the sleeve outer surface 10 is not critical and need not be kept small. In the embodiment shown in FIG. 1a this distance can be made larger. If the distance between the inner wall of the reactor and the outer wall of the sleeve is larger than the uncompressed cleaning device 16 diameter a cleaning device holder could be provided connected to the inner wall 14 of the reactor 12" which cleaning device holder is configured for holding the elongated cleaning device 16 along the sleeve 8 and towards the sleeve outer surface 10. Hereby the cleaning device 16 will be transferred over the sleeve outer surface when either the reactor 12" or the sleeve 8 is rotating around the longitudinal axis A.

Keeping a distance between an outer surface of the sleeve 10; 10' and an inner surface of the reactor 14; 14' small is beneficial when treating opaque liquids and as described above problems may arise when using long sleeves made from fused quartz. In order to keep this distance small and still provide enough space for a cleaning device the reactor 12; 12' in both the embodiment shown in FIG. 1b and the embodiment shown in FIG. 2 has a partly circular cross-sectional shape with at least one part having an extended inner and outer radius where the at least one cleaning device 16; 16' is provided.

Describing the design and position of the reactor in the embodiments of FIGS. 1b and 2, the reactor 12; 12' can be said to be concentric with the sleeve 10; 10' when ignoring the at least one part having an extended radius, i.e. the part or parts of the reactor not having an extended radius has a cross sectional shape being a part of a circle which circle is centered around the central longitudinal axis A.

In some embodiments of the invention (shown in FIGS. 1b and 2) the reactor 12; 12' comprises for each cleaning device 16; 16' a first part 18; 18' having a cross sectional shape being essentially a part of a circle which circle is centered around the longitudinal axis A and a second part 20; 20' connected to the first part 18; 18' and configured for holding the cleaning device 16; 16'. An inner surface 14a; 14a' of the first part 18; 18' and an inner surface 14b; 14b' of the second part 20; 20' together encircle the outer surface 10; 10' of the sleeve 8; 8'. The inner surface 14b; 14b' of the second part 20; 20' being provided at a greater distance from the outer surface 10; 10' of the sleeve 8; 8' than the inner surface 146a; 14a' of the first part 18; 18' is. The second part 20; 20' is hereby the part of the reactor 12; 12' having an extended radius as referred to above. The second part 20; 20' in combination with the cleaning device 16; 16' can also be referred to as a cleaning arrangement 17; 17'. If two cleaning devices 16; 16' are provided, one for one part of the sleeve length and another for another part of the sleeve length as shown in FIG. 3 one first part 18; 18' and one second part 20; 20' will be provided separately for each cleaning device 16; 16'. If on the other hand two cleaning devices 16; 16' are provided each for the whole length of the sleeve but opposite each other the reactor 12; 12'; 12" has to be designed a bit differently than what is shown in FIGS. 1b and 2. Two second parts 20; 20' may be provided for housing the two cleaning devices.

The distance between the outer surface 10; 10' of the sleeve 8; 8' and the inner surface 14; 14' of the reactor 12; 12'; 12" needs sometimes to be kept small especially when treating opaque liquids in order to allow the UV light to reach as much as possible of the liquid volume passing though the liquid treatment system. At those parts of the reactor 12; 12' not having extended radius, i.e. between the sleeve outer surface 10; 10' and the first part 18; 18' of the reactor 12; 12', an average of this distance can be for example between 1 and 10 mm. Due to the tolerances when producing a sleeve from fused quartz (also called fused silica) as described above the distance will often vary. Thanks to the extended radius of the reactor 12; 12' where the cleaning device 16; 16' is provided cleaning of the sleeve outer surface can be performed while still keeping a thin treatment chamber 4, i.e. a small distance between sleeve outer surface and inner surface of the reactor as described above.

FIG. 9a shows a cleaning device 16" according to one embodiment of the invention. In this embodiment the cleaning device 16" is a metal braid. The metal braid is a tubular, hollow cylinder which is braided, knitted or woven from a metallic material. Furthermore the metal braid is abrasive and the metallic material is suitably resistant to UV light and corrosion. One example of metallic material which can be used for the metal braid is stainless steel. Other examples are Monel and Titanium. In one embodiment of the invention the metal braid is elastic in itself.

Another example of a cleaning device 16 to be used in systems according to the invention is shown in FIG. 9b. In this embodiment an elastic tube is provided inside the metal braid. The elastic, inner tube provides elasticity to the cleaning device 16 which is important for the cleaning efficiency. Furthermore liquid flow through the cleaning device 16 can be avoided by providing an inner tube. Liquid flow through the metal braid decrease performance of the reactor. Both systems shown in FIGS. 1a and 1b are shown with a cleaning device 16 comprising a metal braid with an elastic tube inside as the one shown in FIG. 9b. However other cleaning devices as described in this text can be used in the embodiments shown in both FIGS. 1a and 1b.

FIGS. 10a and 10b show a reactor 12 according to one embodiment of the invention comprising the two different cleaning devices 16, 16" as shown in FIGS. 9a and 9b.

FIG. 1b shows schematically a transversal cross section of a liquid treatment system 2 according to one embodiment of the invention. Most parts have been described above. In this embodiment a hollow cylindrical metal braid comprising an inner tube is used as the cleaning device 16. The reactor 12 comprises a first part 18 having a cross section being a part of a circle which is centered around the same longitudinal axis A around which the sleeve 8 also is centered. The reactor 12 comprises further a second part 20 which is connected to the first part 18 such that inner walls 14a of the first part 18 and inner walls 14b of the second part 20 together encircle the sleeve 8. The inner wall 14b of the second part 20 is provided at a greater distance from the sleeve 8 than the inner wall 14a of the first part 18. Furthermore the cleaning device 16 is provided between the second part 20 and the sleeve 8. The cleaning device 16 is compressed towards the sleeve 8 by the inner walls of the second part 20. The second part 20 can also be said to have an extended radius compared to the rest of the reactor 12. In this embodiment it can be seen that the second part 20 is connected to the first part 18 by two fasteners 31, such as screws. In another embodiment the second part 20 can be either connected to the first part 18 by other means, such as a clamp, soldering or gluing or the second part 20 and the first part 18 could instead be molded together or be extruded as one part.

FIG. 2 shows schematically some details in a transversal cross section of a liquid treatment system according to another embodiment of the invention. The UV lamp 6 is not shown here. A reactor 12' is provided around the sleeve 8'. The reactor 12' comprises a first part 18' and a second part 20'. Inner walls 14b' of the second part 20' are provided at a greater distance from the sleeve outer surface 10' than inner walls 14a' of the first part 18' of the reactor 12'. Furthermore the elongated cleaning device 16' housed within the second part 20' is not a hollow cylinder in this embodiment but comprises an elongated cleaning part 16a' from abrasive material provided closest to the outer surface 10' of the sleeve 8' and an elongated elastic part 16b' provided closest to the inner surface 14' of the reactor 12'. The cleaning part 16a' can be a metal braid or steel wool and the elastic part 16b' can be a spring, foam rubber, silicon rubber or a flexible tube.

In another embodiment of the invention the elongated cleaning device 16; 16' comprises an elongated elastic part which is both elastic and abrasive, such as an elastic metal braid as described above.

Figure 6:
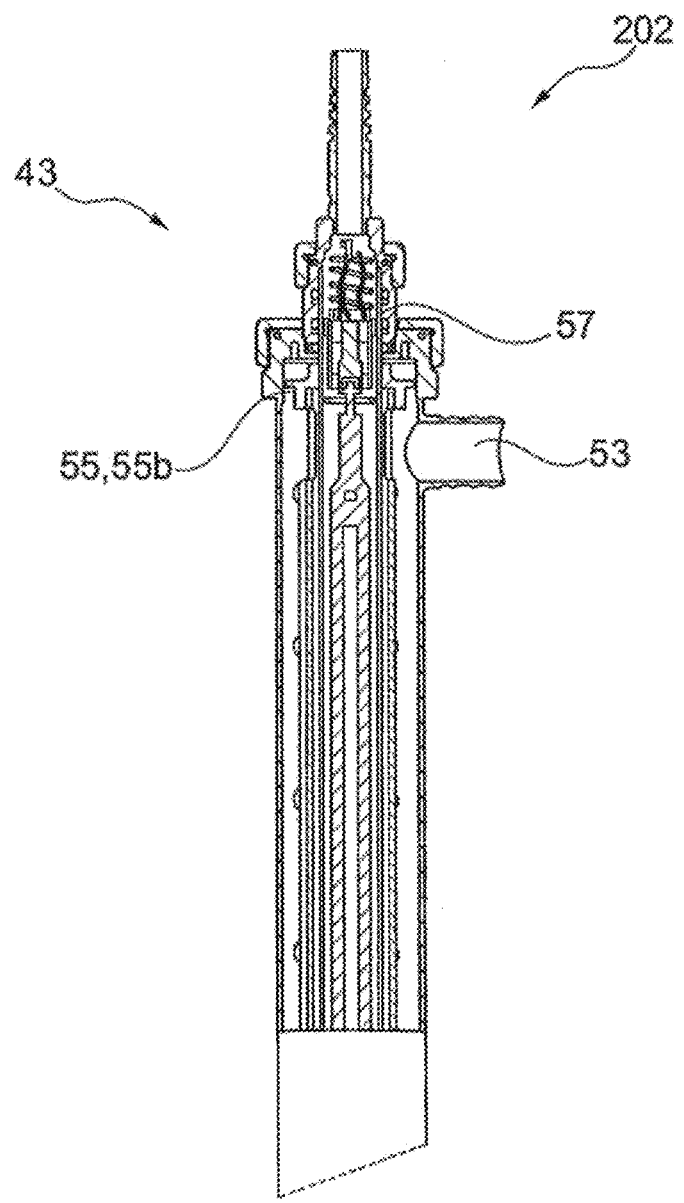
FIG. 6 is a side view, partly in cross section of the same liquid treatment system as shown in FIGS. 4 and 5 but showing the opposite end, a second end, of the liquid treatment system.

FIGS. 4-8 show a first end 41 and a second end 43 partly in cross section of a liquid treatment system 202 according to one embodiment of the invention. The reactor 12 can be seen enclosing the sleeve 8. An outer chamber 45 is in this embodiment provided enclosing the reactor 12. Liquid can be provided into the system through a liquid inlet 47 provided in the outer chamber 45. The reactor 12 comprises openings 49 such that liquid entering the system from the liquid inlet 47 can be transferred into the treatment chamber 4 which is provided between the reactor 12 and the sleeve 8. In this embodiment it can be seen that the reactor 12 is connected to a driving mechanism 51 for rotating the reactor. However in another embodiment the sleeve could instead be rotated. FIG. 6 is showing the second end 43 of the system. An outlet 53 is provided at this end.

In some embodiments of the invention the liquid treatment system 202 further comprises a surface bearing arrangement 55 configured for keeping the sleeve 8 and the reactor 12 axially and radially aligned while allowing at least one of the sleeve 8 and the reactor 12 to rotate around the longitudinal axis A. Such a surface bearing arrangement can be designed in different ways. Bearings can be provided at different positions in the system for keeping the sleeve and the reactor in correct position. Furthermore, if an outer chamber is provided in the system enclosing the reactor the bearings can also keep the reactor and the sleeve in position within the outer chamber. In some embodiments of the invention the reactor and the sleeve can be removed from the outer chamber for maintenance, for example change of cleaning device. In that case the bearings need to be designed for allowing removal of the reactor. This is provided in the embodiment shown in FIGS. 4-8.

In the embodiment shown in FIGS. 4-8 the surface bearing arrangement 55 comprises four separate bearings 55a, 55b, 55c, 55d. This is best seen in FIGS. 7-8. A first bearing 55a is provided at a first end 41 of the system. The first bearing 55a is an annular bearing provided around the reactor 12 and connected to the reactor. The first bearing is arranged to cooperate with and seal against an inner wall 61 provided inside the outer chamber 45. Flow of liquid between the reactor and the outer chamber is hereby limited by the first bearing 55a. The central position of the reactor 12 within the outer chamber 45 is ensured by this inner wall 61. However the reactor 12 can still be removed and inserted into the outer chamber 45 and therefore the first bearing 55a is provided for sealing and correct positioning. A second bearing 55b is provided at a second end 43 of the system and is an annular bearing provided around the reactor and connected to the reactor. In this embodiment the second bearing 55b is provided at an upper (referring to directions in drawings) end of the reactor and designed to protrude outside the reactor and hold the sleeve which is protruding outside the reactor centered within the reactor. The second bearing 55b can also comprise a part which is protruding out to the walls of the outer chamber in order to keep the reactor centered within the outer chamber. Furthermore a third bearing 55c and a fourth bearing 55d are provided at the first end of the system. The fourth bearing 55d is provided for keeping a lowermost end of the reactor 12 (referring to directions in the drawing) and a lowermost end of the sleeve 8 in relative positions to each other and for transferring the rotation from the driving mechanism 51 to the reactor 12. The third bearing 55c is provided for keeping the reactor 12 centered within the outer chamber 45. The sleeve 8 is also kept in a centered position at the second end 43 of the system by a sleeve holder 57.

By this surface bearing arrangement 55 the reactor 12 and the sleeve 8 can be kept in position within an outer chamber 45 also during rotation for cleaning of the sleeve surface by the cleaning device 16. Furthermore the reactor and the sleeve can be removed for maintenance without the need to drain the whole system from the liquid.

The invention claimed is:

1. A liquid treatment system, comprising:
    at least one ultra-violet (UV) light treatment lamp arranged within an elongated protective UV-transparent sleeve provided along a central longitudinal axis A, said elongated protective UV-transparent sleeve having an outer surface and an essentially circular cross-sectional shape; and
    an elongated reactor configured to receive said elongated protective UV-transparent sleeve, whereby an elongated liquid treatment chamber for receiving liquid to be treated, is provided between an inner surface of the elongated reactor and the outer surface of the elongated protective UV-transparent sleeve; and
    at least one elongated cleaning device provided side by side with the elongated protective UV-transparent sleeve within the elongated liquid treatment chamber and along at least a part of a length of the elongated protective UV-transparent sleeve,
    wherein said at least one elongated cleaning device is compressed towards the outer surface of the elongated protective UV-transparent sleeve by the elongated reactor, and wherein at least one of the elongated protective UV-transparent sleeve and the elongated reactor is configured to rotate around the central longitudinal axis A such that the at least one elongated cleaning device will be touching and cleaning the outer surface of the elongated protective UV-transparent sleeve over essentially a whole circumference of the elongated protective UV-transparent sleeve,
    wherein the elongated reactor has a partly circular cross-sectional shape with at least one part having an extended inner and outer radius where the at least one elongated cleaning device is provided.

2. The liquid treatment system according to claim 1, wherein the elongated reactor comprises, for each cleaning device:
    a first part having a cross sectional shape being essentially a part of a circle, which circle is centered around the central longitudinal axis A, and
    a second part configured for holding the cleaning device and connected to the first part,
    wherein an inner surface of the first part and an inner surface of the second part together encircle the outer surface of the elongated protective UV-transparent sleeve, wherein the inner surface of the second part being provided at a greater distance from the outer surface of the elongated protective UV-transparent sleeve than the inner surface of the first part is.

3. The liquid treatment system according to claim 1, wherein either the elongated protective UV-transparent sleeve or the elongated reactor is rotated either in one direction or back and forth around the central longitudinal axis A, such that the at least one elongated cleaning device will be touching and cleaning the outer surface of the elongated protective U-transparent sleeve over the whole circumference of the elongated protective UV-transparent sleeve.

4. The liquid treatment system according to claim 1, further comprising a surface bearing arrangement configured for keeping the elongated protective UV-transparent sleeve and the elongated reactor axially and radially aligned while allowing at least one of the elongated protective UV-transparent sleeve and the elongated reactor to rotate around the central longitudinal axis A.

5. The liquid treatment system according to claim 1, wherein two cleaning devices are provided, one cleaning device of the two cleaning devices being for one part of the length of the elongated protective UV-transparent sleeve and another cleaning device of the two cleaning devices being for a remainder part of the length of the elongated protective UV-transparent sleeve, whereby the two cleaning devices are provided diametrically opposite each other within the elongated reactor, one on each side of the elongated protective UV-transparent sleeve.

6. The liquid treatment system according to claim 1, wherein two cleaning devices are provided, one cleaning device of the two cleaning devices being on one side of the elongated protective UV-transparent sleeve and another cleaning device of the two cleaning devices being on an opposite side of the elongated protective UV-transparent sleeve.

7. The liquid treatment system according to claim 1, wherein the at least one elongated cleaning device comprises a metal braid.

8. The liquid treatment system according to claim 7, wherein the metal braid is a hollow cylinder which is braided, knitted or woven from a metallic material.

9. The liquid treatment system according to claim 8, wherein the metal braid is abrasive and the metallic material is resistant to UV light and corrosion.

10. The liquid treatment system according to claim 8, wherein the metallic material is stainless steel, monel or titanium.

11. The liquid treatment system according to claim 7, wherein the metal braid is a hollow cylinder and comprises an elastic inner tube.

12. The liquid treatment system according to claim 1, wherein the elongated cleaning device comprises an elongated cleaning part from abrasive material provided closest to the outer surface of the elongated protective UV-transparent sleeve and an elongated elastic part provided closest to the inner surface of the elongated reactor.

13. The liquid treatment system according to claim 12, wherein the elongated cleaning part is a metal braid or steel wool, and the elongated elastic part is a spring, foam rubber, silicon rubber or a flexible tube.

14. The liquid treatment system according to claim 1, wherein the elongated cleaning device comprises an elongated elastic, abrasive material.

* * * * *